(12) United States Patent
Lafond (10) Patent No.: US 6,328,082 B1
(45) Date of Patent: Dec. 11, 2001

(54) DISPOSABLE STERILE BAG, E.G. FOR BREAST MILK

(75) Inventor: Danielle Lafond, Beloeil (CA)

(73) Assignee: BBtresor Inc., Ste-Julie (CA)

( * ) Notice: Subject to any disclaimer, the term of this patent is extended or adjusted under 35 U.S.C. 154(b) by 0 days.

(21) Appl. No.: 09/521,181

(22) Filed: Mar. 7, 2000

(51) Int. Cl.$^7$ ....................................................... B65B 1/04
(52) U.S. Cl. ........................ 141/313; 141/114; 604/346; 215/11.3; 215/11.6
(58) Field of Search .................................. 141/114, 313, 141/98; 383/91, 71; 604/74–76, 346, 347; 215/11.1–11.6

(56) References Cited

U.S. PATENT DOCUMENTS

| | | | |
|---|---|---|---|
| 4,356,954 | * | 11/1982 | Mojonnier ................................ 383/91 |
| 4,501,585 | * | 2/1985 | Friedman ............................... 604/346 |
| 4,634,006 | * | 1/1987 | Yanase .................................... 383/44 |
| 4,950,236 | * | 8/1990 | Wilson ..................................... 604/74 |
| 6,050,432 | * | 4/2000 | Koehnke ................................ 215/11.3 |

* cited by examiner

*Primary Examiner*—Steven O. Douglas
(74) *Attorney, Agent, or Firm*—Swabey Ogilvy Renault (57) ABSTRACT

A disposable sterile plastic bag includes a liquid receiving chamber which can be accessed upon removal of a tear off strip for introducing therein liquids, such as breast milk. The bag also includes a closure member to close the bag once filled with milk. The bag further includes indicia thereon for indicating the volume of milk in the bag, and an extension away from the chamber so that information about the milk can be provided, e.g. by writing, on the bag without danger of piercing the bag. Once opened, the bag can be attached to an outlet port of a breast pump such that pumped milk is conveyed directly and sterilely into the bag, and the bag can then be stored in sub-ambient temperature until ready to be fed to a baby, at which time the bag is opened, the closure is cut off from the bag and the bag is installed on, and used as a liner for, a bag holder which is provided with a cap and nipple and acts as a feeding bottle.

26 Claims, 8 Drawing Sheets

DISPOSABLE STERILE BAG, E.G. FOR BREAST MILK

BACKGROUND OF THE INVENTION

1. Field of the Invention

The present invention relates to flexible bags and, more particularly, to sterile disposable plastic bags for use in handling various liquids.

2. Description of the Prior Art

Various bags have been developed for the sterile transportation and/or storage of samples in the medical and food fields, such as human fluid samples, milk, water in environmental studies, etc.

Figure 3:
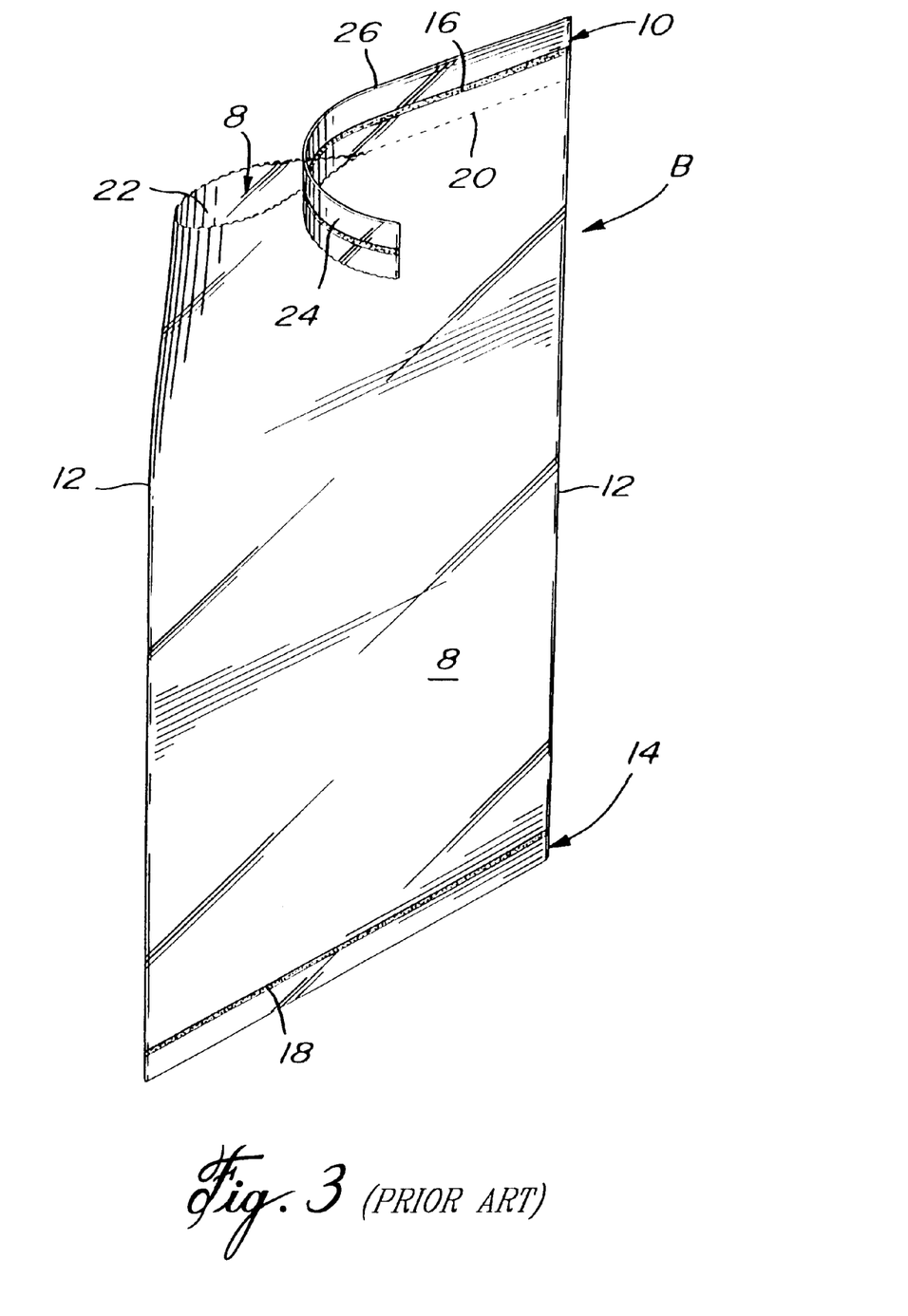
FIG. 3 is a perspective view of a conventional sterile plastic bag adapted to hold therein liquid samples, wherein the sterile bag is shown in a partly open position.

Such a plastic bag is disclosed in U.S. Pat. No. 5,564,829 issued on Oct. 15, 1996 to Lafond. As seen in FIG. 3, in this patent a disposable sterile plastic bag B comprises a two-ply sheet flexible material consisting of front and rear sheets 8 integrally joined at opposed side edges 12, 12 thereof (or the bag may be made from a tube) and including opposite upper and lower ends 10 and 14, respectively. The front and rear sheets 8, 8 are joined at the upper and lower ends 10 and 14 thereof respectively by upper and lower heat seals 16 and 18, respectively, with a sealed sample receiving chamber being defined between the two plastic sheets 8, 8 inwardly of the bag's side edges 12, 12 and upper and lower sealed ends 16 and 18. Inwardly of the upper seal 16, there is defined a tear-off line 20 transversely across the two sheets 8,8 and parallelly to the upper seal 16 thereby forming a detachable strip 24 outwardly of the tear-off line 20. The tear off line 20 is punctured through both sheets 8 across the upper end 10 of the bag B and lower than the upper heat seal 16 such that the upper heat seal 16 extends substantially parallelly between the tear off line 20 and an upper edge 26 of the bag B. When the liquid sample is ready to be introduced in the bag B, the strip 24 is removed from the bag B by pulling it so as to cause rupture of the two sheets 8, 8 at the tear-off line 20. The bag's chamber is thus sterile when the sample is introduced therein and the bag B, when so opened, defines a mouth 22 through which the liquid sample may be introduced in the bag B. The bag's sterility does not depend on how the bag is packaged or on the integrity of the packaging's seal as the bag is itself sterile until the strip 24 is removed therefrom, that is until the bag B is ready to be used.

Such plastic bags may also include near an open end thereof a wire or metal strip which is mounted transversely across the bag with ends extending past the side edges of the bag. Once the bag has been filled with the sample to be transported/stored, the open end is folded at least once over the bag about the wire or metal strip so as to close the open end and the ends of the wire or metal strip are then folded at the side edges of the bag and brought around so as to extend inwardly behind the bag. This safely and effectively encloses the sample in the plastic bag.

SUMMARY OF THE INVENTION

It is therefore an aim of the present invention to provide a novel sterile bag for holding therein liquids.

It is also aim of the present invention to provide a novel sterile bag having indicia thereon for allowing a user to determine at least approximately the volume of liquid in the bag.

It is a further aim of the present invention to provide a novel sterile bag which includes an extension outside of the bag's liquid receiving chamber and adapted to be allow the user to provide, such as by writing, information thereon, for instance data regarding the liquid stored in the bag.

It is a still further aim of the present invention to provide a sterile bag in combination with a breast pumping device, wherein breast milk delivered by the pumping device is conveyed directly and sterilely into the bag, for instance, for storage thereof.

It is a still further aim of the present invention to provide a sterile bag in combination with a feeding bottle where the bag acts as a bottle liner, whereby there is no transfer of milk from the storage bag to the feeding bottle bag.

Therefore, in accordance with the present invention, there is provided a disposable sterile plastic bag in combination with a breast pumping device, said bag being adapted to contain breast milk and to be fluidly connected to said pumping device, said pumping device being adapted for retrieving breast milk from a human breast such that said breast milk is directed into said bag, said bag comprising a flexible closed enclosure means defining a chamber adapted to contain therein the breast milk received from said pumping device, said enclosure means being permanently sealed except at one portion thereof which comprises bag access means adapted to substantially seal said bag in a first position thereof but also adapted to selectively allow in a second position thereof the breast milk to be introduced in said chamber when it is desired to use said bag, whereby once in said second position the breast milk can be received in said bag with said bag is fluidly connected to said pumping device.

Also in accordance with the present invention, there is provided a disposable sterile plastic bag in combination with a bag holder, said bag being adapted to contain milk, said bag holder comprising a hollow body and a cap provided with a nipple and being adapted for feeding a baby, said bag holder being adapted for receiving therein said bag, said bag comprising a flexible closed enclosure means defining a chamber adapted to contain milk therein, said enclosure means being permanently sealed except at one portion thereof which comprises bag access means adapted to substantially seal said bag in a first position thereof but also adapted to selectively allow in a second position thereof the milk is to be introduced in said chamber when it is desired to use said bag, wherein, once in said second position, a top end of said bag can be folded over an upper end of said bag holder with said cap being engageable to said upper end of said bag holder for imprisoning said top end of said bag between said cap and said upper end of said bag holder such that said bag hangs in said bag holder with milk being introduced in said bag at least one of before and after said bag is inserted in said bag holder and mounted thereto.

Further in accordance with the present invention, there is provided a method of substantially sterilely handling breast milk, comprising the steps of:

a) providing a disposable sterile bag;

b) fluidly connecting said bag to an outlet of a breast pumping device; and c) retrieving breast milk from a human breast by way of said pumping device and conveying the breast milk directly from said outlet into said bag.

Still further in accordance with the present invention, there is provided a method of substantially sterilely handling breast milk, comprising the steps of:

a) providing a disposable sterile bag comprising a tear off strip and providing a bag holder;

b) removing said tear off strip to reveal a milk receiving chamber of said bag; and c) mounting said bag to said bag holder;

wherein milk is introduced in said bag between said steps b) and c) or after step c).

Still further in accordance with the present invention, there is provided a disposable bag in combination with a breast pumping device, said bag being adapted to contain breast milk and to be fluidly connected to said pumping device, said pumping device being adapted for retrieving breast milk from a human breast, said bag comprising an enclosure means defining a chamber adapted to contain therein the breast milk received from said pumping device, said enclosure means defining an opening for allowing the breast milk to be introduced in said chamber, whereby, when said bag is fluidly connected to said pumping device, the breast milk pumped by said pumping device is directed into said bag.

BRIEF DESCRIPTION OF THE DRAWINGS

Having thus generally described the nature of the invention, reference will now be made to the accompanying drawings, showing by way of illustration a preferred embodiment thereof, and in which.

DESCRIPTION OF THE PREFERRED EMBODIMENTS

FIG. 3 illustrates a conventional sterile plastic bag B made for instance from heavy-gauge transparent polyethylene. More particularly, the bag B can be made from an elongated sleeve which is transversely cut so as to obtain a bag of desired length or height, that is the distance between the opposed open ends of the severed sleeve. Such a construction produces a bag having no side seams which reduces the costs of manufacture of the bag B and increases the efficiency of the protection afforded by the bag B. Then, the bottom end of the severed sleeve is closed, for example, by heat sealing thereby producing a bag having an open upper end. This upper end, in the present invention, is temporarily sealed by a further heat seal which is carried out between the upper edge of the bag and a tear off line defined transversely across the bag at its upper end, whereby when the bag is required for holding a sample, for instance in a laboratory blender, the tear off strip defined between the tear off line and the upper edge of the bag can be detached from the latter. With this construction, the bag remains substantially and sufficiently sterile until it is used, that is until the tear off strip is removed therefrom.

The bag B is initially produced and sold in a sealed position where the tear off is not detached from the rest of the bag. When a sample or the like must be deposited in the bag B, the bag B is opened by proceeding as illustrated in FIG. 3.

More particularly, in FIG. 3, the bag B is of the two-ply type having identical front and rear sheets 8 integrally joined at side edges 12 thereof and having opposite upper and lower ends 10 and 14, respectively. The two sheets 8 are joined in a tight sealed manner at the upper end 10 of the bag B by known connection means, such as a heat seal 16. Similarly, the sheets 8 are sealingly joined at the lower end 14 of the bag B by a lower heat seal 18.

A tear off line 20 is punctured through both sheets 8 across the upper end 10 of the bag B and lower than the upper heat seal 16 such that the upper heat seal 16 extends substantially parallelly between the tear off line 20 and an upper edge 26 of the bag B. Therefore, there is a tear off strip 24 defined at the upper end 10 of the bag B which when detached from the remainder of the bag B in a manner initiated in FIG. 3, reveals an open mouth 22 of the bag B through which the bag B can obviously be filled with the sample intended to be stored therein.

Figure 1:
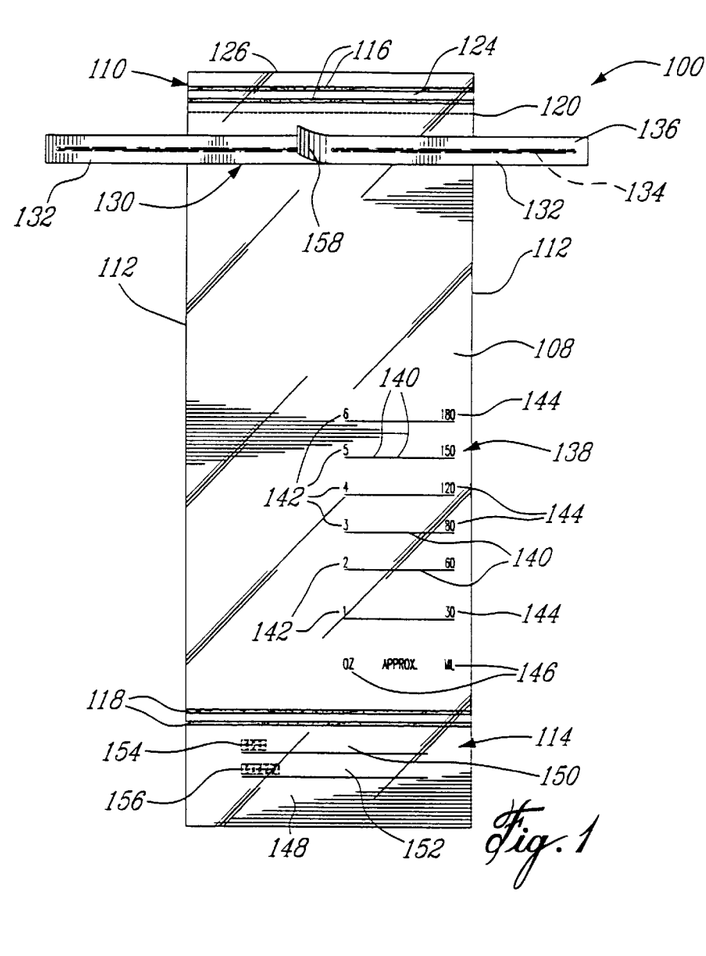
FIG. 1 is a front elevational view of a sterile plastic bag in accordance with the present invention, wherein the sterile bag is shown in a closed or sealed position thereof.
Figure 2:
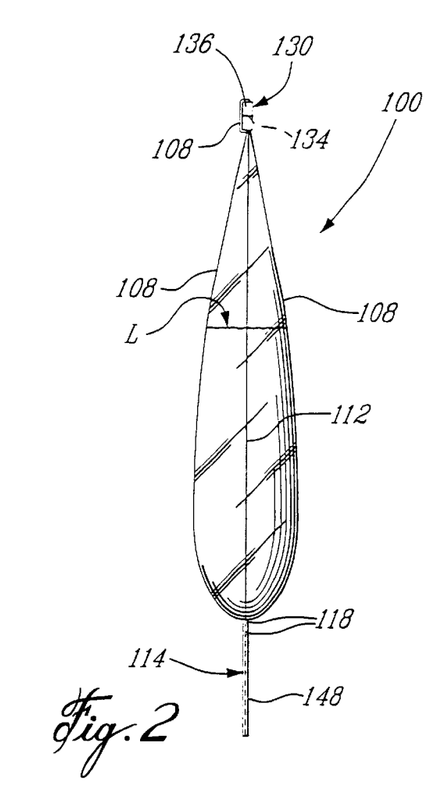
FIG. 2 is a side elevational view of the sterile bag of the present invention which has been opened, filled with a liquid and closed for storing the liquid.

Now turning to the present invention, FIGS. 1 and 2 illustrate a disposable sterile plastic bag 100 for holding therein liquids, for instance breast milk such that it may be stored in the refrigerator or freezer. The bag 100 has a basic structure similar to the conventional bag B of FIG. 3 in that it comprises identical front and rear sheets 108 integrally joined at the side edges 112 thereof, generally as a result of the bag 100 being made from a tube, and having opposite upper and lower ends 110 and 114, respectively. The two sheets 108 are joined in a tight sealed manner at the upper end 110 of the bag 100 by a heat seal 116 with two parallel and spaced heat seals 116 being herein shown. Similarly, the two sheets 108 are sealingly joined at the lower end 114 of the bag 100 by a lower heat seal 118, also herein embodied by a pair of heat seals 118 which ensure total sterility and leakproofness of the bag 100.

A tear off line 120 is punctured through both sheets 108 across the upper end 110 of the bag 100 and lower than the upper heat seals 116 such that the upper heat seals 116 extend substantially parallelly between the tear off line 120 and an upper edge 126 of the bag 100. Therefore, there is a tear off strip 124 defined at the upper end 110 of the bag 100 which when detached from the remainder of the bag 100 (in a manner initiated and shown for the conventional bag B in FIG. 3), reveals an open mouth at the tear off line 120 of the bag 100 through which the bag 100 can obviously be filled with, for instance, the breast milk intended to be stored in the bag 100. The tear off strip 124 preserves the sterility of the bag 100 until its manipulation.

The bag 100 further includes near the mouth thereof, that is just below the tear off line 120, a closure member 130 which is mounted transversely across the bag 100 with ends 132 (acting as pull-tabs) of the closure member 130 extending past the side edges 112 of the bag 100. The closure member, in a known manner, includes a pair of metal strips or wires 134 (one disposed outwardly on each of the front and rear sheets 108) and a pair of adhesive tapes 136 disposed outwardly over the metal wires 134 to attach the metal wires 134 to the front and rear sheets 108 of the bag 100 with the tapes 136 adhering to the bag 100 inwardly of the side edges 112 thereof while adhering together outwardly of the side edges 112. The closure member 130 allows for the bag 100 to be repeatedly opened and closed without risk of loss of contents.

At least one of the front and rear sheets 108 of the bag 100 is provided thereon, for instance by printing, with indicia 138 which indicate the approximate volume of liquid (e.g. breast milk) in the bag 100. Calibrated reference marking 140 indicate liquid levels whereas scales of volumes, in ounces 142 and in millimeters 144, are associated with each reference marking 140 such that the user can easily determine approximately the volume of liquid being poured, or having been previously put or now remaining, in the bag 100. Opposite each scale of volume indicia 142 and 144, there is provided an indication of the volume measurement unit 146 (i.e. "OZ" for ounces and "ML" for millimeters) associated with each scale.

Also, the lower end 114 defines an extension 148 of dimensions sufficient to allow for some information to be provided on the bag 100 regarding the contents thereof. The extension 148 is basically comprised of the lower ends of both the front and rear sheets 108, that the portions thereof extending below the lower heat seals 118 (although the extension could include a single layer, such as either one of the front and rear sheets 108). Various information may be provided, for instance by writing, on the extension 148, such as the date of bagging on line 150 and the volume of liquid (e.g. breast milk) on line 152 with references 154 and 156 reading, in such a case, as "DATE" and "VOLUME", respectively.

Importantly, as the extension 148 is located outwardly of, that is not opposite to, the liquid containing chamber of the bag 100 (see FIG. 2), there is no risk or damaging or piercing the bag 100 when writing information at areas 150 and 152 of the extension 148, and thus there is no risk of causing a leak in the bag 100. The extension 148 being planar, it is possible to easily write thereon even after the bag 100 has been filled with liquid.

Therefore, once the tear off strip 124 has been removed from the bag 100, the bag 100 may be opened by spreading side pull-tabs 158 (one such pull-tab extending outwardly from the middle of each adhesive tape 136) thereby avoiding contamination of the inside of the bag 100. Then, the liquid (breast milk) may be inserted in the bag 100 while allowing space in the bag 100 for expansion of the liquid if, for instance, it is intended to be frozen. The longitudinal ends or pull-tabs 132 of the closure member 130 (i.e. its portions extending outwardly beyond the side edges 112 of the bag 100) are then pulled away so as to draw the front and rear sheets 108 together opposite the closure member 130 thereby substantially closing the upper mouth of the bag 100. After, pressure is applied on the outside of the bag 100 to remove trapped air. The closure member 130 is then rolled down, for instance four (4) times over, and the longitudinal ends 132 of the closure member 130 are folded inwardly, at the side edges 112 of the bag 100, over either the front and rear sheets 108 to prevent the "unrolling" of the closed upper end of the bag 100. This safely and effectively encloses the liquid in the plastic bag 100. In FIG. 2, the bag 100 so contains a liquid, such as breast milk, with a level thereof being indicated at L.

Using a regular ball point pen, the user may indicate, for instance, date and volume information on lines 150 and 152 of the extension 148 located at the bottom of the bag 100.

When one is ready to use the breast milk stored in the bag 100, it possible to use the bag 100 as a bottle liner with Playtex™-type feeding bottles of the type having a cylindrical configuration and open opposite longitudinal ends, the upper end having outside threads screwably engageable by inside threads of a bottle cap provided with a nipple, wherein a bag is typically introduced in the feeding bottle and the upper end of the bag is folded outwardly over the upper end of the feeding bottle and the outside threads thereof such that, when the bottle cap is subsequently engaged to the feeding bottle the folded over upper end of the plastic bag is imprisoned between the outside threads of the feeding bottle and the inside threads of the bottle cap.

When the bag 10 filled with milk is used with such Playtex™-type feeding bottles, the bag 100 is first completely unrolled and then the upper end of the bag 100 is cut, below the closure member 130. The rest of the bag 100 containing the breast milk is then inserted in the feeding bottle and the upper end of the bag 100 is peeled outwardly over the upper rim of the feeding bottle, in a conventional manner, covering completely the outside threads of the feeding bottle, whereafter the bottle cap (and its nipple) are screwed onto the feeding bottle and the bag.

Therefore, the milk does not have to be transferred from any storage container into the conventional bag used with the feeding bottle, thereby eliminating possible contamination of the breast milk.

Furthermore, milk pumped from the breast using, for instance, a breast pump, may be fed directly into the bag 100 thereby again eliminating a transfer from the standard container attached to the pump to a storage container. Indeed, milk may be pumped directly into the bag 100 which can then be used for storage purposes and thereafter used as a bottle liner, as described hereinabove. For this, the bag 100 is attached to the outlet of the pumping unit, e.g. its transfer hose, by using the closure member 130 which is brought around the outlet and tied thereat by twisting together the longitudinal ends 132 of the closure member 130. Then, the pump may be activated and the resulting pumped breast milk is conveyed into the bag 100.

Figures 4A, 4B, 4C:
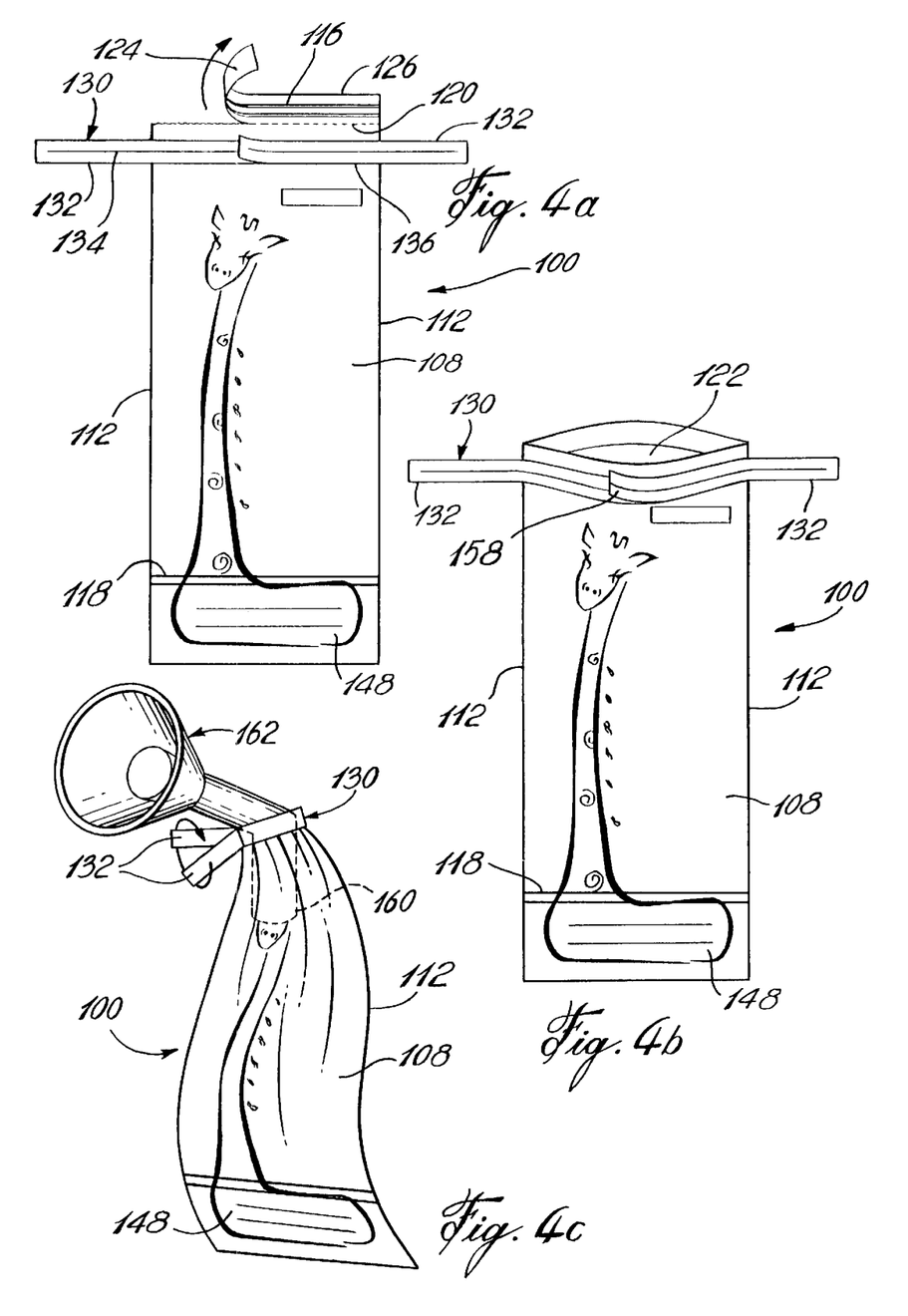
FIGS. 4a to 4i illustrate various steps followed by the bag of FIGS. 1 and 2 when used in a typical cycle.

FIGS. 4a to 4i show the use of the bag 100 through a typical cycle. More particularly, FIG. 4a illustrates the removal of the safety tear off strip 124 from the bag 100. FIG. 4b show the outward pulling of side pull-tabs to open the bag 100 and define an upper open mouth 122 therefor. FIG. 4c illustrates an outlet tip 160 of a breast pump 162 inserted in the mouth 122 of the bag 100 with the closure member 130 being wrapped around the outlet tip 160 and the longitudinal ends 132 of the closure member 130 being shown as they are being tied together by twisting such as to secure the upper end of the bag 100 to the outlet tip 160 of the breast pump 162; once milk has been expressed from the breast into the bag 100, the ends 132 of the closure member 130 are untwisted and detached from each other thereby allowing the filled bag 100 to be removed from the breast pump 162.

Figure 4D:
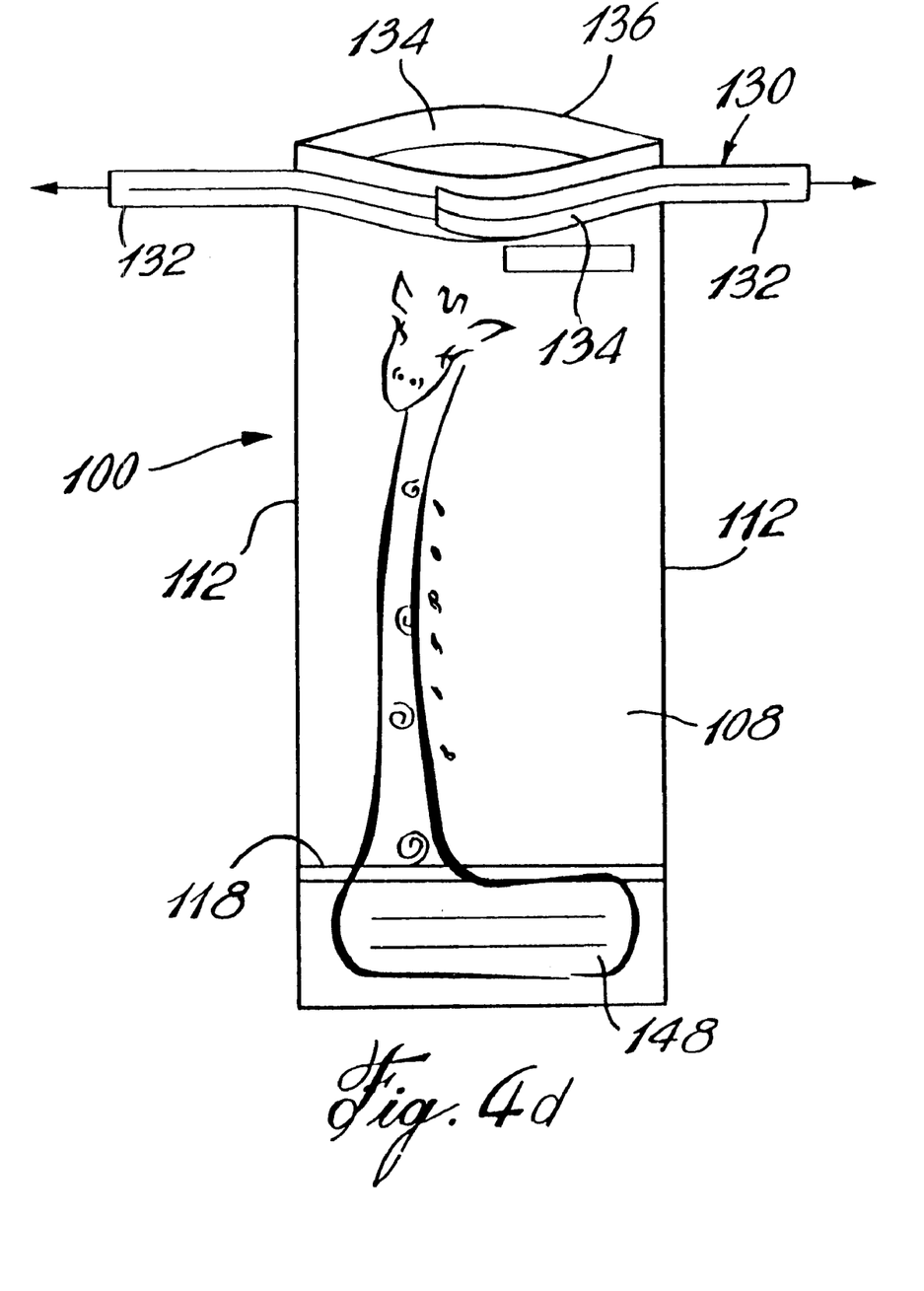
Figure 4E:
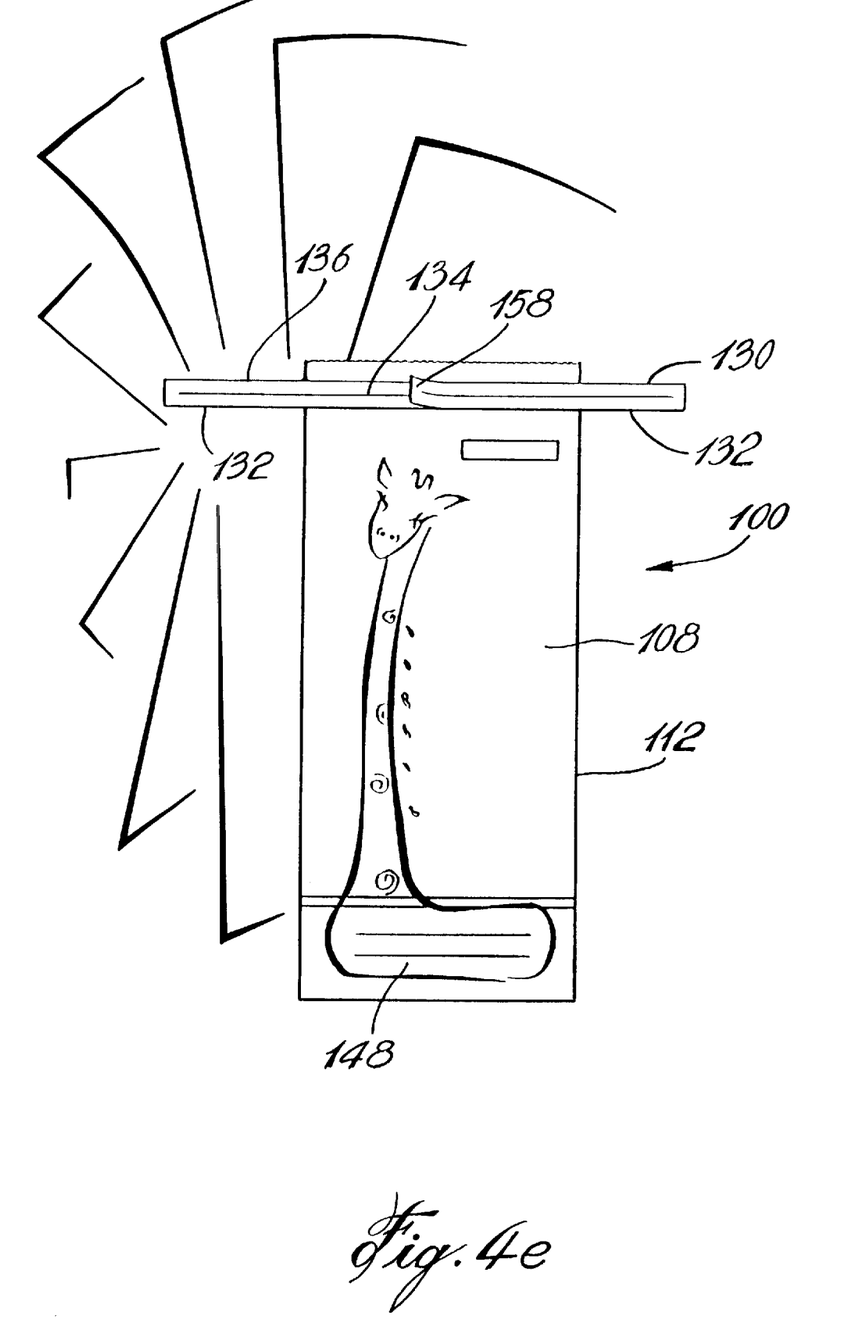
Figure 4F:
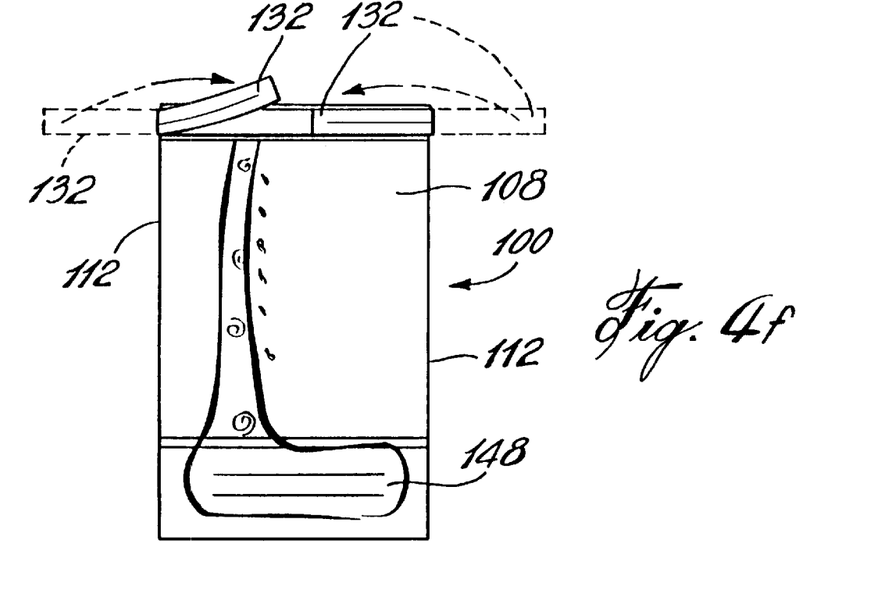

As seen in FIG. 4d, the longitudinal ends 132, now acting as pull tabs, are then pulled away from each other to close the mouth 122 of the bag 100 with air being removed from the bag 100 by pressing with one's fingers on the outside of both the front and rear sheets 108. In FIG. 4e, the bag 100, while being firmly held by the longitudinal ends 132 of the closure member 130, is rotated e.g. 4 or 5 times) about the closure member 130 to close the upper end of the bag 100. FIG. 4f illustrates the longitudinal ends 132 being folded inwardly substantially about the side edges 112 of the bag 100 to "lock" the rolled-up upper end of the bag 100 and so provide a leakproof seal.

Figure 4G:
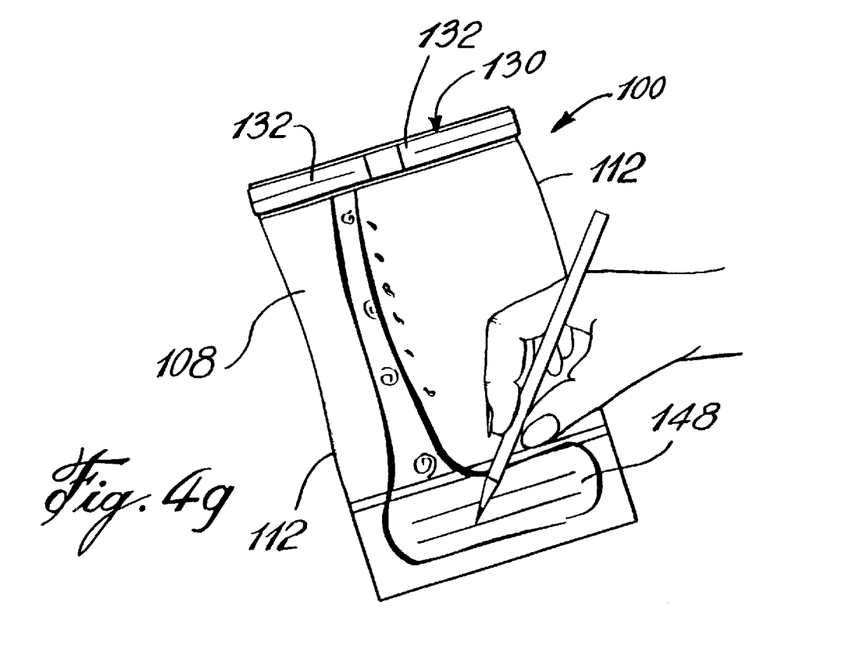
Figure 4H:
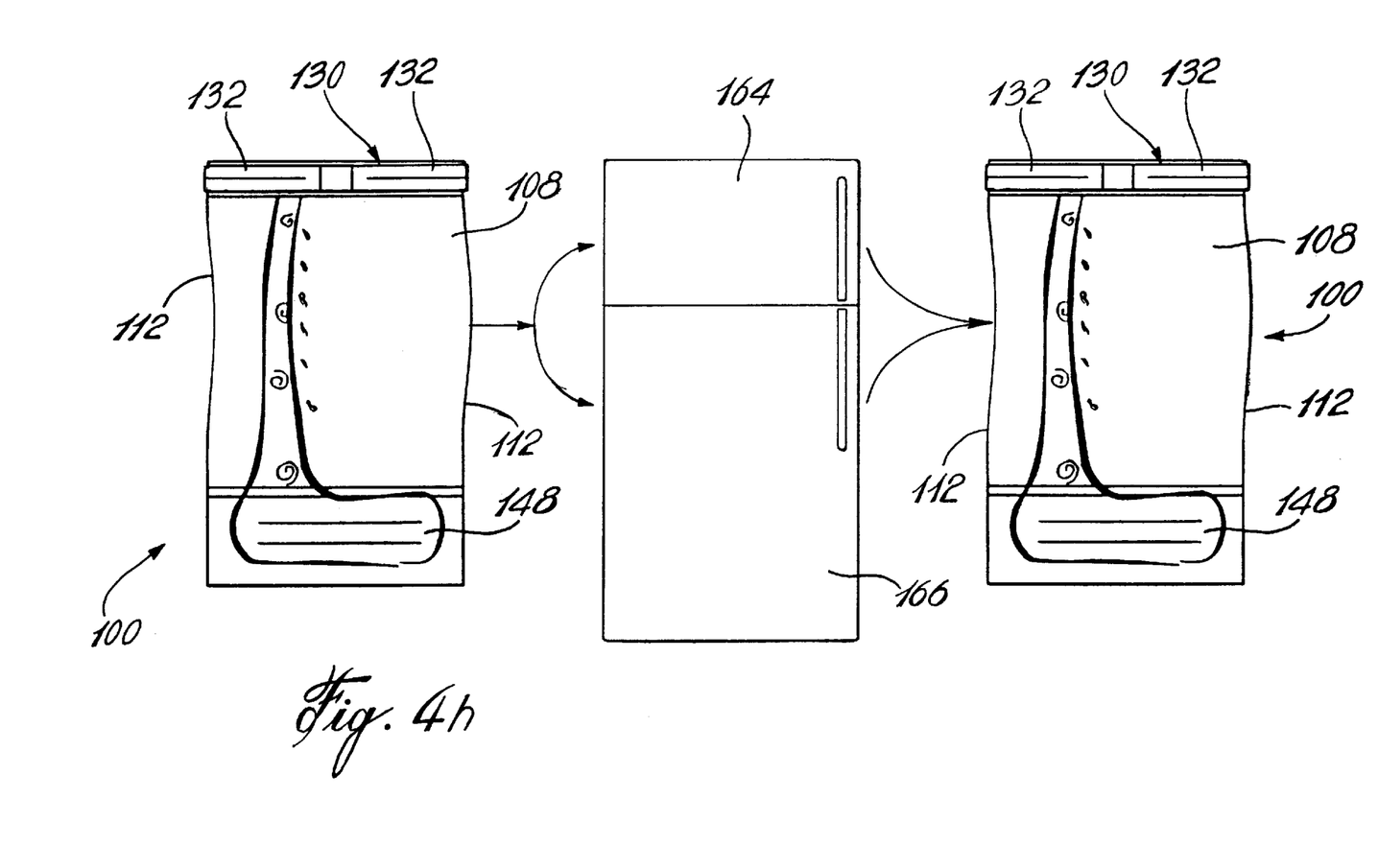
Figure 4I:
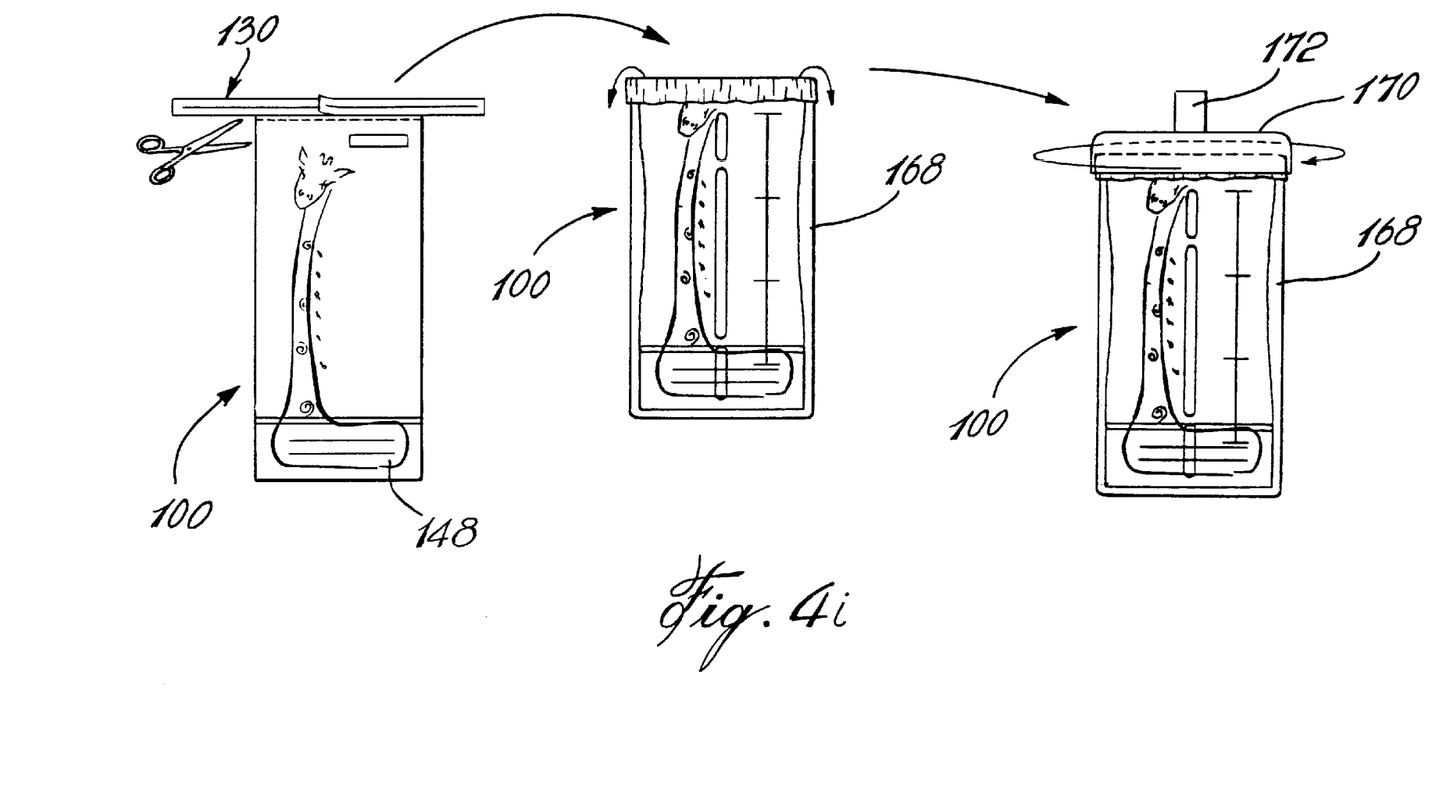

FIG. 4g shows the writing of the extraction date and extracted milk volume at areas 150 and 152 of the extension 148. FIG. 4h illustrates the milk being stored in a freezer 164 or refrigerator 166 and then being taken out therefrom generally for consumption of the frozen or cold milk. Finally, FIG. 4i shows the bag 100 being used as a disposable liner for a feeding bottle 168, wherein the bag 100 is first cut just under its closure member 130 (see left image in FIG. 4i) with the bag section carrying the closure member 130 being discarded and with the remainder of the bag being inserted in the feeding bottle 168; this is followed by the upper end of the bag being folded outwardly over the upper rim of the bottle 168 (see middle image in FIG. 4i), and then by a bottle cap 170 (provided with a nipple 172) being screwed onto the upper end of the bottle 168 thereby imprisoning the folded upper end of the bag between the bottle 168 and the bottle cap 170.

I claim:

1. A disposable bag adapted to contain breast milk, comprising a flexible closed enclosure defining a chamber adapted to contain therein breast milk, said enclosure being permanently sealed except at one portion thereof which comprises a bag access adapted to substantially seal said bag in a first position thereof but also adapted to selectively allow in a second position thereof the breast milk to be introduced in said chamber when it is desired to use said bag, whereby once in said second position the breast milk can be received in said bag, wherein said bag comprises a section located remote from said enclosure and adapted for receiving thereon information about a content of said bag.

2. A disposable bag as defined in claim 1, wherein said section comprises at least a first area for indicating thereon a date of filling of said enclosure with breast milk.

3. A disposable bag as defined in claim 2, wherein said section also comprises a second area for indicating thereon a volume of breast milk introduced in said enclosure.

4. A disposable bag as defined in claim 1, wherein said bag is made from a plastic tube permanently closed at a lower end thereof by lower a seal thereby delimiting a bottom end of said enclosure, said section extending from said lower seal away from said enclosure.

5. A disposable sterile plastic bag in combination with a breast pumping device, said bag being adapted to contain breast milk and to be fluidly connected to said pumping device, said pumping device being adapted for retrieving breast milk from a human breast such that said breast milk is directed into said bag, said bag comprising a flexible closed enclosure defining a chamber adapted to contain therein the breast milk received from said pumping device, said enclosure being permanently sealed except at one portion thereof which comprises a bag access adapted to substantially seal said bag in a first position thereof but also adapted to selectively allow in a second position thereof the breast milk to be introduced in said chamber when it is desired to use said bag, whereby once in said second position the breast milk can be received in said bag with said bag being fluidly connected to said pumping device, wherein said bag comprises a closure member adapted, with an outlet end of said pumping device extending into said bag, for detachably mounting said bag to said pumping device such that breast milk retrieved by said pumping device is directly delivered through said outlet end into said bag.

6. A disposable bag in combination with a pumping device as defined in claim 1, wherein said bag defines opposite said enclosure indicia for providing an indication of a volume of breast milk contained in said chamber.

7. A disposable bag in combination with a pumping device as defined in claim 1, wherein said closure member is further adapted for temporarily closing said access once breast milk has been introduced in said chamber.

8. A disposable bag in combination with a pumping device as defined in claim 7, wherein said closure member is adapted to be detachably mounted around said outlet end of said pumping device.

9. A disposable bag in combination with a pumping device as defined in claim 8, wherein said access comprises a detachable strip including an upper seal for sealing said bag in said first position but adapted to be removed from said bag with said detachable strip in said second position thereby opening said bag at said one portion thereof for subsequent receipt of the breast milk therein, and wherein said closure member is located inwardly of said detachable strip such as to remain on said bag when said detachable strip is removed therefrom.

10. A disposable bag in combination with a pumping device as defined in claim 9, wherein said enclosure comprise front and rear rectangular sheets joined at opposed side edges thereof and at a bottom end thereof, said strip being provided at an upper end of said sheets for substantially sealing in said first position said chamber defined between said sheets, said strip comprising a tear off line extending inwardly of said upper seal and between said upper seal and said closure member, whereby in said second position said strip is detached from said upper end of said enclosure at said tear off line with said upper seal being removed therefrom with said strip thereby allowing access to said chamber.

11. A disposable bag in combination with a pumping device as defined in claim 9, wherein said closure member comprises on each side of said enclosure an adhesive tape and a metal wire both extending transversely of said bag and having respective longitudinal ends thereof extending outwardly past longitudinal side edges of said bag, said metal wire being held onto said bag by said adhesive tape, both said adhesive tapes being adhesively attached together at said longitudinal ends thereof provided outwardly of each of said side edges of said bag such that, to close said access, an upper end of said bag is rolled up around said closure member and then said longitudinal ends of said adhesive tapes and of said metal wires are folded inwardly over said enclosure to prevent said upper end from unrolling.

12. A disposable bag in combination with a pumping device as defined in claim 11, wherein each said adhesive tape is provided with a lateral pull tab located opposite said enclosure such that said bag can be opened at said access by pulling outwardly on both lateral pull tabs in opposite directions.

13. A disposable bag in combination with a pumping device as defined in claim 7, further in combination with a bag holder which comprises a cap provided with a nipple and which is adapted for feeding a baby, said bag holder being hollow, said bag being exempt of an upper end thereof including said closure member and thereby now defining a top end, said bag holder being adapted for receiving therein said bag containing breast milk therein, said top end being adapted to be folded over an upper end of said bag holder with said cap being engageable to said upper end of said bag holder for imprisoning said top end of said bag between said cap and said upper end of said bag holder.

14. A disposable bag in combination with a pumping device as defined in claim 13, wherein an outside wall of said upper end of said bag holder comprises outside threads adapted to threadably engage inside threads defined on an inside wall of said cap.

15. A disposable sterile plastic bag in combination with a bag holder and with a breast pumping device, said bag being adapted to contain milk, said bag holder comprising a hollow body and a cap provided with a nipple and being adapted for feeding a baby, said bag holder being adapted for receiving therein said bag, said bag comprising a flexible closed enclosure defining a chamber adapted to contain milk therein, said enclosure being permanently sealed except at one portion thereof which comprises a bag access adapted to substantially seal said bag in a first position thereof but also adapted to selectively allow in a second position thereof the milk to be introduced in said chamber when it is desired to use said bag, wherein, once in said second position, a top end of said bag can be folded over an upper end of said bag holder with said cap being engageable to said upper end of said bag holder for imprisoning said top end of said bag between said cap and said upper end of said bag holder such that said bag hangs in said bag holder with milk being introduced in said bag at least one of before and after said bag is inserted in said bag holder and mounted thereto, said bag in said second position being adapted to be fluidly connected to said pumping device, said pumping device being adapted for retrieving breast milk from a human breast such that said breast milk is directed into said chamber, wherein said bag comprises a closure member adapted, with an outlet end of said pumping device extending into said bag, for detachably attaching said bag to said pumping device such that breast milk retrieved by said pumping device is directly delivered through said outlet end into said bag.

16. A disposable sterile plastic bag in combination with a bag holder and with a breast pumping device as defined in claim 15, wherein said access comprises a detachable strip including an upper seal for sealing said bag in said first position but adapted to be removed from said bag with said detachable strip in said second position thereby opening said bag at said one portion thereof for subsequent receipt of milk therein, and wherein an outside wall of said upper end of said bag holder comprises outside threads adapted to threadably engage inside threads defined on an inside wall of said cap.

17. A disposable sterile plastic bag in combination with a bag holder and with a breast pumping device as defined in claim 16, wherein said bag comprises a closure member for temporarily closing said access, in said second position, once milk has been introduced in said chamber, said closure member being located inwardly of said detachable strip such as to remain on said bag when said detachable strip is removed therefrom.

18. A disposable sterile plastic bag in combination with a bag holder, said bag being adapted to contain milk, said bag holder comprising a hollow body and a cap provided with a nipple and being adapted for feeding a baby, said bag holder being adapted for receiving therein said bag, said bag comprising a flexible closed enclosure defining a chamber adapted to contain milk therein, said enclosure being permanently sealed except at one portion thereof which comprises a bag access adapted to substantially seal said bag in a first position thereof but also adapted to selectively allow in a second position thereof the milk to be introduced in said chamber when it is desired to use said bag, wherein, once in said second position, a top end of said bag can be folded over an upper end of said bag holder with said cap being engageable to said upper end of said bag holder for imprisoning said top end of said bag between said cap and said upper end of said bag holder such that said bag hangs in said bag holder with milk being introduced in said bag at least one of before and after said bag is inserted in said bag holder and mounted thereto, wherein said bag comprises a section located remote from said enclosure and adapted for receiving thereon information about a content of said bag.

19. A disposable sterile plastic bag in combination with a bag holder and with a breast pumping device as defined in claim 15, wherein said bag defines opposite said enclosure indicia for providing an indication of a volume of breast milk contained in said chamber.

20. A disposable sterile plastic bag in combination with a bag holder and with a breast pumping device as defined in claim 15, wherein said closure member is further adapted for temporarily closing said access once breast milk has been introduced in said chamber.

21. A method of substantially sterilely handling breast milk, comprising the steps of:

a) providing a disposable sterile bag comprising a closure member;

b) fluidly connecting said bag to an outlet of a breast pumping device with said closure member being used to attach said bag to said outlet; and c) retrieving breast milk from a human breast by way of said pumping device and conveying the breast milk directly from said outlet into said bag.

22. A method as defined in claim 21, further comprising the following steps: d) closing said bag containing the breast milk and storing it in sub-ambient temperature; and, once one wants to use the breast milk to feed a baby, e) removing said bag from said sub-ambient temperature, f) opening said bag and g) installing said bag on a bag holder provided with a nipple for feeding the baby.

23. A method as defined in claim 22, wherein, in step d), said bag is closed using said closure member; and wherein, between said steps e) and g) said closure member is removed from said bag.

24. A method as defined in claim 21, wherein said bag comprises a tear off strip to retain said bag sterile until ready for use, wherein, prior to step b), said tear off strip is removed from said bag thereby revealing a milk receiving chamber of said bag, and wherein, in step b), said outlet is positioned such as to extend to said chamber.

25. A method of substantially sterilely handling breast milk, comprising the steps of:

a) providing a closed disposable sterile bag comprising a tear off strip and providing a bag holder;

b) removing said tear off strip to reveal a milk receiving chamber of said bag; and c) mounting said bag to said bag holder;

wherein milk is introduced in said chamber between said steps b) and c) or after step c).

26. A method as defined in claim 25, wherein after step b), said bag is attached to a breast pumping device such that breast milk retrieved by said pumping device is directly delivered through into said bag.

* * * * *